United States Patent [19]

Hellstrom et al.

[11] 4,087,694
[45] May 2, 1978

[54] TOMOGRAPHY SYSTEM

[75] Inventors: Melbourne J. Hellstrom, Severna Park; Laverne R. Bunch, Baltimore; Henri Froger, Bethesda, all of Md.

[73] Assignee: CGR Medical Corporation, Baltimore, Md.

[21] Appl. No.: 724,641

[22] Filed: Sep. 20, 1976

[51] Int. Cl.² ............................................. G03B 41/16
[52] U.S. Cl. ................................. 250/445 T; 250/402; 250/491
[58] Field of Search ............... 250/445 T, 445 R, 490, 250/491, 401, 402

[56] References Cited

U.S. PATENT DOCUMENTS 3,809,886  5/1974  Cochran ........................... 250/445 T Primary Examiner—Craig E. Church
Attorney, Agent, or Firm—Brady, O'Boyle & Gates

[57] ABSTRACT

A linear tomographic method and apparatus wherein an overhead tube-stand or X-ray tube unit is non-mechanically coupled to a bucky or X-ray film holder to produce linear tomographs. No physical attachment exists between the tube-stand and the bucky. The tube-stand position is sensed by electro-magnetic radiation and more particularly by light radiation which is generated by a laser and directed to a reflector attached to the tube-stand adjacent to the tube focal spot. Light energy is reflected therefrom and sensed by an interferometer which produces a tube-stand position signal which is used to generate a command signal to operate respective drive motors which translate the bucky in an opposite direction to the tube-stand and simultaneously rotate the X-ray tube so that the X-ray focal spot, center of film, and imaginary fulcrum point remain substantially colinear during a tomographic sweep.

21 Claims, 1 Drawing Figure

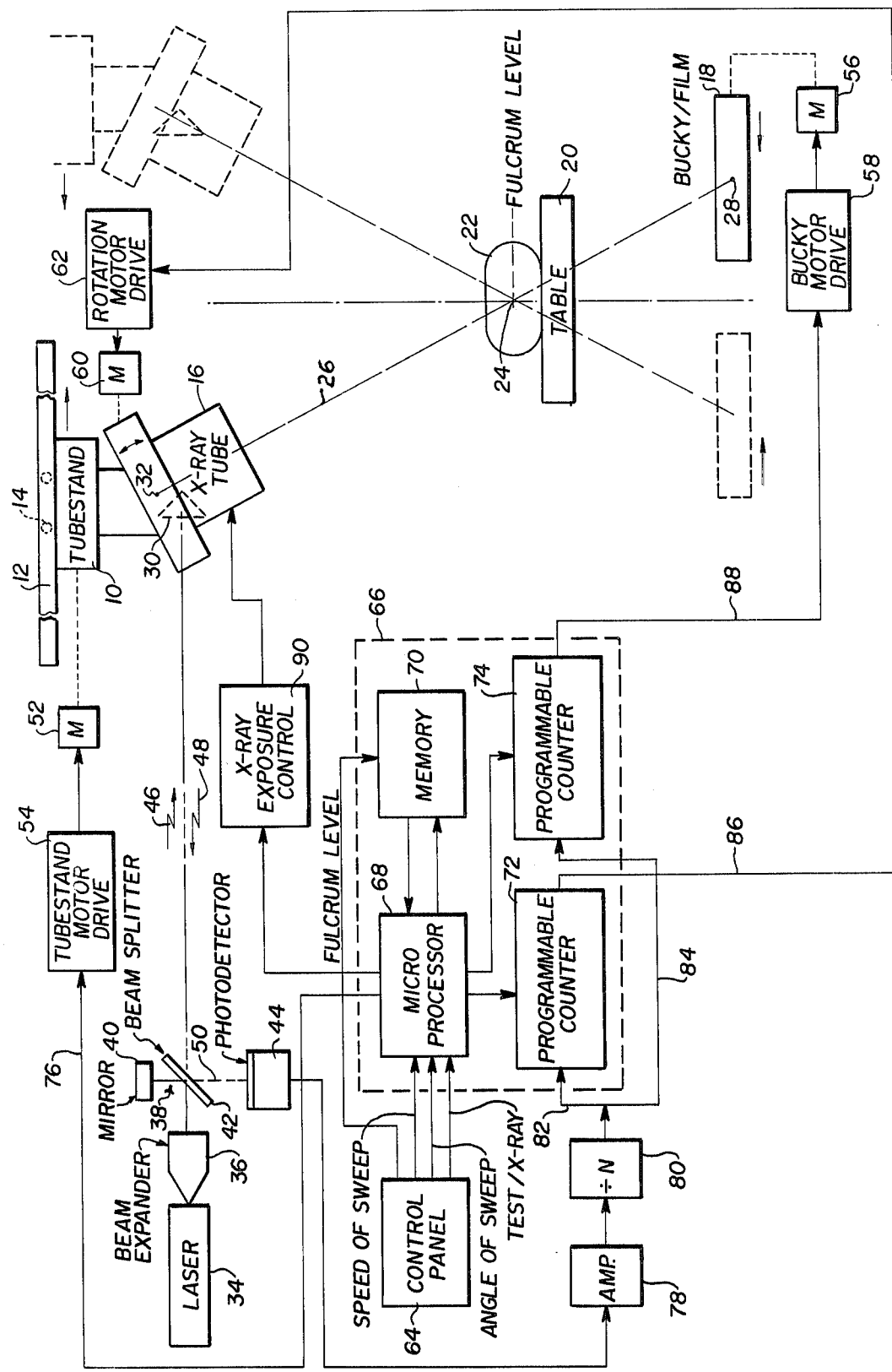

TOMOGRAPHY SYSTEM

BACKGROUND OF THE INVENTION

This invention relates generally to tomography and more particularly to an electronic linear tomography system which eliminates the need for the conventional mechanical coupling between an overhead tube suspension and a bucky in an X-ray table.

Present linear tomographic attachments for state of the art radiographic tables require a mechanical linkage between the tube suspension system and the bucky which is further fixed at one point in space with respect to the table. Motion of the tube suspension system then causes the focal spot to move in one direction, the bucky proportionately in the opposite direction, and the tube to rotate so that the central ray approximately points to the same point on the film located on the bucky. During non-tomographic radiographic procedures, this mechanical linkage is in the way of the operating personnel and has to be removed in some manner or another. This is generally troublesome and accordingly a system which obviates the mechanical linkage would provide a substantial convenience and improvement compared with conventional mechanical systems in that little, if any, set-up time or tear-down time would be required. In addition, mechanical linkages may produce unwanted vibration resulting in unsatisfactory tomographic films.

SUMMARY

Accordingly, it is an object of the present invention to provide improvement in linear tomography systems and briefly comprises a method and means for non-mechanically coupling the X-ray source to the film during a tomographic procedure and includes a source of electromagnetic radiation directed to the X-ray source for sensing the position and translation of the source and generating control signals in accordance with the sensed translation to translate the film proportionately in the opposite direction and additionally rotate the X-ray source so that the central ray therefrom rotates about the focal spot of the source and always points approximately to the same location on the film. In a specific illustrative embodiment, a helium-neon laser directs a beam of monochromatic optical light through an interferometer to a retroreflector for sensing the position of the X-ray tube's focal spot at a place which is fixed relative to the focal spot whereupon the reflected light is directed back to the interferometer which produces a moving interference fringe pattern output which corresponds to the linear translation of the X-ray tube. An electrical pulse train is generated from the output of a photodetector exposed to the fringe pattern which is utilized to generate a motor drive signal for an electrical motor coupled to the bucky/film which translate linearly in an opposite direction with respect to the X-ray tube. Simultaneously, a motor drive signal is generated for operating a rotational drive motor coupled to the X-ray tube.

DESCRIPTION OF THE DRAWING

The drawing constitutes an electromechanical block diagram illustrative of the preferred embodiment of the subject invention.

DESCRIPTION OF THE PREFERRED EMBODIMENT

Referring now to the drawing, reference numeral 10 denotes an X-ray tube suspension system commonly referred to as a tube-stand which for example is mounted for translational movement on a ceiling rail assembly 12 including a plurality of rollers 14 or the like. An X-ray tube 16 is rotatably mounted on the tube-stand 10 and is directed to a movable X-ray film holder or bucky 18 located on the opposite side (underside) of an X-ray table 20 upon which a patient 22 or other object under examination is located. As is well known in a tomographic procedure, the tube-stand 10 including the X-ray tube 16 and the bucky 18 which contains the X-ray film are moved or translated in opposite linear directions while maintaining a constant point or fulcrum 24 in space within the patient 22 which acts to accurately define an image location 28 on the film of the fulcrum point 24 while blurring the surrounding image regions.

In order to maintain a virtual i.e. a non-mechanical link between the X-ray tube 16 and the bucky 18 so that the X-ray beam 26 always points to the same point 28, the present invention contemplates locating an optical retroreflector 30 at a spot which is fixed relative to the focal spot 32 of the X-ray tube 16. The position and more particularly the linear translation of the tube-stand 10 and accordingly the X-ray tube 16 is sensed by means of a helium-neon laser 34 which produces a monochromatic light beam, for example 6328A, which is directed to the retroreflector 30 through a beam expander 36 and an interferometer assembly 38 including a mirrow 40, a beam splitter 42, and an interference fringe pattern sensor comprising a photodetector 44.

The transmitted laser beam 46 passing through the beam splitter 42 is directed to the retroreflector 30 where it is sent back as a return beam 48. A portion of the laser's output beam impinging on the beam splitter 42 is directed to and reflected from the mirror 40 while the return beam 48 is reflected from one side of the beam splitter 42 which combine to provide an interference fringe pattern signal 50 which is directed to the photodetector 44. For a wavelength of 6328A, the linear translation of the X-ray tube 16 will result in a phase reversal of the fringe pattern for each 0.312mm of linear translation. This phenomenon is adapted to provide a means for providing controlled movement of the bucky 18 as well as rotation of the X-ray tube 16 in response to the movement of the tube-stand 10.

Turning now more particularly to the means for driving the respective elements, the tube-stand 10 is mechanically coupled to an electric drive motor 52 which is electrically coupled to and operated in response to a tube-stand motor drive unit 54. The bucky 18 in turn is mechanically coupled to its own electrical drive motor 56 which is operated in response to the bucky motor drive unit 58. Thus while the tube-stand drive motor 52 is moving the tube-stand 10 linearly in one direction, e.g. forward, the bucky drive motor 56 will operate to move the bucky in the opposite direction while maintaining a fixed colinear relationship with one another through the fulcrum point 24. The fixed colinear relationship, moreover, requires that the X-ray tube 16 rotate during the linear sweep, which may be, for example, one meter (approximately 40 inches). This rotation is provided by a third electrical drive motor 60 mechanically coupled to the X-ray tube 16 and is operated in accordance with the electrical output from a rotation motor drive unit 62.

Control signals for the three motor drive units 54, 58 and 62 are generated in response to predetermined parameters selected by the system operator, e.g. or a radiologist from a control panel 64 which is adapted to provide at least four inputs to the system, namely: (a) fulcrum level, (b) speed of sweep, (c) angle of sweep, and (d) whether or not the forthcoming operational sequence will be a "test" run or an actual tomographic X-ray procedure. Motor drive control signals are generated in accordance with these inputs as well as from the electrical pulse output signals of the photodetector 44 by a self-contained electronic control circuit 66 consisting of, by way of an illustrative example, a microprocessor unit 68, a memory unit 70, and a pair of programmable counters 72 and 74. These last four named elements, 68, 70, 72 and 74 are comprised of solid state integrated circuit devices well known to those skilled in the art. For example, the microprocessor 68 constitutes an off the shelf item such as a MOSTEK, Inc. MK3850 type of device whereas the memory 70 comprises a MOSTEK, Inc. MK3851 type of device. The counters 72 and 74 are MOSTEK, Inc. MK50395 type of devices.

The electronic circuit, for example, microprocessor 68 in combination with the memory 70 performs the calculations in response to the inputs applied thereto from the control panel 64 to first generate commands for the three motors 52, 56 and 60 to assume a preset (START) position as shown in the FIGURE. This is accomplished by the microprocessor 68, sending a command signal over signal conductor means 76 to the tube-stand motor drive unit 54, causing the motor 52 to translate the tube-stand 10, if necessary, back to the preset START position.

Any movement of the tube-stand 10 is correspondingly sensed by the photodetector 44 associated with the interferometer 38, which couples an electrical output pulse signal corresponding to each phase reversal of the fringe pattern detected to an amplifier circuit 78. The amplifier 78 acts to appropriately shape the pulses coupled thereto. Accordingly, a pulse train in the order of $3.2 \times 10^4$ pulses for each centimeter of translation of the tube-stand is generated. The pulse output from the amplifier 78 is fed to a counter/divider circuit 80 wherein a division by N, where for example N = 8, is performed for providing an output having a more readily usable pulse repetition rate. The output of the counter 80 is then coupled to both programmable counters 72 and 74 via signal conductor means 82 and 84.

The microprocessor 68 in accordance with the operator inputs selected, couples a respective control signal to both of the programmable counters 72 and 74 to effect a predetermined pulse division of the respective pulse inputs coupled thereto. The counters 72 and 74 operate to provide a binary command signal on output signal conductor means 80 and 82 which couple to the rotation drive unit 62 and the bucky motor drive unit 58, respectively, causing the bucky 18 to move in an opposite direction at a rate proportional to that of the tube-stand 10 as well as appropriately rotating the X-ray tube 16.

It should be pointed out that the fulcrum level is determined by the interrelationship of the servo type motion of the bucky 18 provided in response to the motion of the tube-stand 10. Accordingly, the fulcrum level selected by the operator causes the memory 70 to couple programming inputs to the microprocessor 68 dependent upon the speed and angle of sweep selected to cause the respective output counts of the programmable counters 72 and 74 to change in the proper relationship of proportional speeds between the X-ray tube and film.

Accordingly, following the tube-stand 10 being driven to a preset START position, the microprocessor commands the tube-stand drive motor unit 54 to move the tube-stand 10 via the motor 52 in, for example, a sinusoidal velocity profile of linear translation which is sensed by the laser position sensing apparatus which establishes an input pulse rate to the programmable counters 72 and 74. The output pulse signals from the programmable counter 74 commands the bucky drive motor 56 to simultaneously translate the bucky 18 in a like sinusoidal velocity profile so that the center of the film, e.g. point 28, remains colinear with respect to the X-ray beam 26. The output signals from the programmable counter 74 on the other hand simultaneously command the tube rotational drive motor 60 to rotate the X-ray tube 16 to maintain the X-ray exposure over the entire film. During this interval, the microprocessor 68 also operates to couple command signals to an X-ray and exposure control unit 84 which acts to control the operation of the X-ray tube 16 to produce a sequence of X-ray exposures during the selected tomographic sweep to produce a relatively sharp focused radiograph of a thin section of the object 22 at the fulcrum level while the section planes above and below the fulcrum level appear blurred on the film located on the bucky 18.

With a helium-neon laser source the interferometer assembly 38, moreover, is adapted to sense tube-stand position with an accuracy in the order of 0.3 microns. Accordingly, bucky positional accuracy relative to the focal spot 32 of the X-ray tube 16 can easily be obtained to within 0.025mm (0.001 inches).

Thus what has been shown and described is a tie-barless linear tomographic system utilizing a laser interferometer to determine the tube-stand position during a tomographic sweep. A high ratio of tube position resolution to film position resolution is provided for a variable fulcrum level system. The capabilities of the present invention are greatly expanded from previous and conventional tomographic apparatus since the mechanical restraints are removed which thereby eliminate the problems inherent in mechanical coupling between the tube-stand and bucky.

While there has been shown and described what is at present considered to be the preferred method and embodiment of the subject invention, modifications thereto will readily occur to those skilled in the art. It is not desired, therefore, that the invention be limited to the specific steps and arrangements shown and described, but it is to be understood that all equivalents, alterations and modifications coming within the spirit and scope of the present invention, are herein meant to be included.

We claim:

1. A method for non-mechanically linking the motions of an X-ray tube unit with an X-ray receptor unit during a tomographic procedure comprising the steps of:

effecting a predetermined motion of one of said units;

sensing via radiant energy a parameter which is a function of the position of said one unit and generating a parameter signal therefrom by directing a source of radiant energy to a reference location, receiving energy reflected therefrom and detecting the difference characteristic between the energy radiated to and the energy received from said reference location;

generating a command signal in response to said parameter signal; and applying said command signal to said other unit for effecting a follower motion of said other unit with respect to said one unit.

2. In apparatus for making tomographs including X-ray tube means and X-ray receptor means, both of which are adapted to move mutually colinearly through a predetermined fulcrum point during a tomographic procedure, the improvement comprising, in combination:

first and second drive means respectively coupled to and being operable to simultaneously move said X-ray tube means and said X-ray receptor means, in response to command signals applied thereto;

first circuit means coupling a motional command signal to one of said first and second drive means in response to at least one input parameter selected for a predetermined operating sequence;

radiant energy sensing means non-mechanically coupled to the means driven by said drive means coupled to first circuit means and providing a position output signal in accordance with the position change of said driven means; and second circuit means coupled to said position output signal and being responsive thereto to provide a motional command signal coupled to the other of said first and second drive means to effect a follower motion of the means driven thereby.

3. A method for non-mechanically linking the motions of an X-ray tube unit with an X-ray film holder unit during a tomographic procedure comprising the steps of:

effecting translational motion of one of said units;

sensing via radiant energy a parameter which is a function of the position of said one unit and generating a parameter signal therefrom by directing a source of radiant energy to a reference location, receiving energy reflected therefrom and detecting the difference characteristic between the energy radiated to and the energy received from said reference location;

generating a command signal in response to said parameter signal; and applying said command signal to said other unit for effecting a colinear position and translational motion in an opposite direction with respect to said one unit.

4. The method as defined in claim 3 wherein said step of sensing a parameter comprises sensing the position change of the focal spot of said X-ray tube unit and generating a position change signal therefrom; and wherein said step of applying said command signal comprises applying said command signal to said X-ray film holder unit.

5. The method as defined by claim 4 wherein said reference location comprises a location which is fixed in relation to the location of said focal spot and wherein said step of sensing the position change of said focal spot comprises:

directing the source of radiant energy to said location which is fixed in relation to the location of said focal spot and receiving energy reflected therefrom; and generating said position change signal as a function of a difference characteristic between the energy radiated to said location and the energy received from said location.

6. The method as defined by claim 4 wherein said sensing step comprises optically sensing the position change of said focal spot.

7. The method as defined by claim 6 wherein said step of optically sensing comprises:

directing a source of monochromatic light to reflector means positioned at said reference location;

interferometrically combining the light energy directed to said reflector means and the light energy received therefrom; and generating said position change signal from the interference fringe pattern resulting from said combining step.

8. The method as defined by claim 4 and additionally generating another command signal in response to said position change signal, and applying said another command signal to said X-ray tube unit for providing a dependent rotation of said X-ray tube during said tomographic procedure.

9. In apparatus for making tomographs including X-ray tube means and X-ray film means, both of which are adapted to move colinearly in mutually opposite directions through a predetermined fulcrum point during a tomographic procedure, the improvement comprising, in combination:

first and second drive means respectively coupled to and being operable to simultaneously translate said X-ray tube means and said X-ray film means, in response to translational command signals applied thereto;

third drive means coupled to and being operable to rotate said tube means in response to a rotational command signal;

first circuit means coupling a translational command signal to one of said first and second drive means in response to at least one input parameter selected for a predetermined operating sequence;

radiant energy sensing means non-mechanically coupled to the means driven by said drive means coupled to first circuit means and providing a position output signal in accordance with the position change of said driven means;

second circuit means coupled to said position output signal and being responsive thereto to provide a translational command signal coupled to the other of said first and second drive means to effect a follower translation of the means driven thereby; and third circuit means coupled to said position output signal and being responsive thereto to provide a said rotational command signal coupled to said third drive means.

10. The apparatus as defined by claim 9 wherein said radiant energy sensing means comprises an energy source providing a directive output beam of energy, and means located on said means driven by said first circuit means for reflecting said beam of energy directed thereto from said energy source, and means responsive to the reflective beam for providing said position output signal.

11. The apparatus as defined by claim 10 wherein said energy source comprises a source of electromagnetic radiation.

12. The apparatus as defined by claim 11 wherein said source of electromagnetic radiation comprises a source of optical radiation.

13. The apparatus as defined by claim 12 wherein said optical source comprises a laser.

14. The apparatus as defined by claim 9 wherein said one drive means comprises said first drive means and said other drive means comprises said second drive means.

15. The apparatus as defined by claim 14 wherein said radiant energy sensing means comprises optical energy sensing means.

16. The apparatus as defined by claim 15 wherein said optical energy sensing means comprises:
 a source of optical radiant energy located in the vicinity of said X-ray tube means;
 optical energy reflector means located on said X-ray tube means and being in a fixed position relative to the focal spot of said X-ray tube means;
 interferometer means positioned intermediate said optical source and said reflector means and being adapted to output an interference fringe pattern developed from optical energy directed to and reflected from said reflector means in response to translation of said X-ray tube means; and
 means responsive to said interference fringe pattern to provide a pulse signal output in accordance with the phase reversals of the optical energy contained in said interference fringe pattern.

17. The apparatus as defined by claim 16 wherein said first and third drive means comprises a respective electrical motor and motor drive circuit therefor coupled to said X-ray tube means for providing translation and rotation respectively; and
 wherein said second drive means comprises an electrical motor and a motor drive circuit therefor coupled to said X-ray film means for providing translation thereof.

18. The apparatus as defined by claim 17 wherein said first circuit means comprises control circuit means coupled to said X-ray tube translation motor drive circuit; and
 wherein said second and third circuit means have inputs respectively coupled to and responsive to said pulse signal output from said sensing means and being operable in response to respective control signals coupled thereto from said control circuit means to provide respective operating signals coupled to said motor drive circuit means for translating said X-ray film means and said motor drive circuit means for rotating said X-ray tube means respectively.

19. The apparatus as defined by claim 18:
 wherein said control circuit means comprises a circuit including a microprocessor and a memory intercoupled thereto and being operative in response to operator selected fulcrum level, speed of sweep, and angle of sweep to command a predetermined translation of said X-ray tube means by said motor drive circuit therefor; and
 wherein said second and third circuit means comprises programmable pulse counter means responsive to said respective control signals from said microprocessor to provide a predetermined division of said pulse signal output applied thereto for providing said respective operating signals to effect a translation in the opposite direction of said X-ray film means at a proportional speed with respect to that of said X-ray tube means and a predetermined X-ray tube rotation.

20. The apparatus as defined by claim 19 wherein said means responsive to said interference fringe pattern comprises photodetector means located adjacent said interferometer means.

21. The apparatus as defined by claim 20 and additionally including:
 amplifier means coupled to and responsive to said pulse signal output from said photodetector means for shaping the waveform of said pulse signal output; and
 counter means coupled to the output of said amplifier means and being adapted to divide the number of pulses in said pulse signal output by a predetermined factor prior to coupling to said counter means comprising said second and third circuit means.

* * * * *